US 9,200,995 B2

(12) United States Patent
Ahola et al.

(10) Patent No.: US 9,200,995 B2
(45) Date of Patent: Dec. 1, 2015

(54) METHOD AND APPARATUS FOR MONITORING AIR FILTER CONDITION

(71) Applicant: ABB Oy, Helsinki (FI)

(72) Inventors: Jero Ahola, Lappeenranta (FI); Jussi Tamminen, Lappeenranta (FI); Tero Ahonen, Lappeenranta (FI)

(73) Assignee: ABB TECHNOLOGY OY, Helsinki (FI)

( * ) Notice: Subject to any disclaimer, the term of this patent is extended or adjusted under 35 U.S.C. 154(b) by 400 days.

(21) Appl. No.: 13/749,403

(22) Filed: Jan. 24, 2013

(65) Prior Publication Data
US 2013/0197826 A1  Aug. 1, 2013

(30) Foreign Application Priority Data
Jan. 30, 2012  (EP) .................... 12153017

(51) Int. Cl.
G01N 15/08 (2006.01)
B01D 46/00 (2006.01)
B01D 46/44 (2006.01)
H01L 21/67 (2006.01)
F24F 11/00 (2006.01)
F04D 27/00 (2006.01)
F24F 3/16 (2006.01)

(52) U.S. Cl.
CPC .......... G01N 15/082 (2013.01); B01D 46/0086 (2013.01); B01D 46/444 (2013.01); F04D 27/001 (2013.01); F24F 3/161 (2013.01); F24F 11/0078 (2013.01); F24F 11/0079 (2013.01); H01L 21/67253 (2013.01); Y02B 30/746 (2013.01)

(58) Field of Classification Search
CPC ............. G01N 15/082; B01D 46/0086; B01D 46/444; F04D 27/00; H01L 21/67253; F24F 11/0078; F24F 3/161; Y02B 30/746
USPC ......... 702/44; 318/268; 454/187, 52; 415/17, 415/26, 30, 47
See application file for complete search history.

(56) References Cited

U.S. PATENT DOCUMENTS

| 4,786,295 A | 11/1988 | Newman et al. | |
| 5,243,732 A * | 9/1993 | Koharagi et al. | 15/319 |
| 6,241,463 B1 * | 6/2001 | Bahner et al. | 415/17 |
| 6,448,896 B1 * | 9/2002 | Bankus et al. | 340/607 |

(Continued)

FOREIGN PATENT DOCUMENTS

| DE | 10 2005 023 371 A1 | 11/2006 |
| EP | 1 800 919 A2 | 6/2007 |
| EP | 2799789 A1 * | 11/2014 |

OTHER PUBLICATIONS

European Search Report dated Jun. 19, 2012.

Primary Examiner — Carol S Tsai
(74) Attorney, Agent, or Firm — Buchanan Ingersoll & Rooney PC

(57) ABSTRACT

A method and apparatus are disclosed for monitoring accumulation of dirt on an air filter of a ventilation system including the filter and a fan controlled by a frequency converter. An initial value for an operating parameter is determined. A present operating point is determined based on a characteristic curves, and the mechanical power and rotational speed of the fan. A present value for the operating parameter is determined based on the present operating point, and accumulation of dirt is determined on the air filter based on the initial and present values of the operating parameter.

16 Claims, 3 Drawing Sheets

(56) References Cited

U.S. PATENT DOCUMENTS

| | | | |
|---|---|---|---|
| 6,582,295 B1 * | 6/2003 | Abouchaar | 454/158 |
| 6,607,435 B2 * | 8/2003 | Yokoyama et al. | 454/187 |
| 6,755,734 B2 * | 6/2004 | Yokoyama et al. | 454/187 |
| 6,825,632 B2 * | 11/2004 | Hahn et al. | 318/599 |
| 6,997,684 B2 * | 2/2006 | Hahn et al. | 417/44.1 |
| 7,013,950 B2 * | 3/2006 | Steneby et al. | 165/11.1 |
| 7,633,250 B2 * | 12/2009 | Sato | 318/268 |
| 8,823,312 B2 * | 9/2014 | Hessert et al. | 318/700 |
| 2003/0040269 A1 * | 2/2003 | Yokoyama et al. | 454/52 |
| 2003/0045226 A1 * | 3/2003 | Yokoyama et al. | 454/187 |
| 2005/0188842 A1 | 9/2005 | Hsieh et al. | |
| 2005/0247194 A1 | 11/2005 | Kang et al. | |
| 2007/0146148 A1 | 6/2007 | Kawasaki et al. | |
| 2012/0031139 A1 * | 2/2012 | Shirota et al. | 62/426 |

* cited by examiner

METHOD AND APPARATUS FOR MONITORING AIR FILTER CONDITION

RELATED APPLICATION(S)

This application claims priority under 35 U.S.C. §119 to European Patent Application No. 12153017.4 filed in Europe on Jan. 30, 2012, the entire content of which is hereby incorporated by reference in its entirety.

FIELD

The disclosure relates to air filter condition monitoring, and for example, to accurately estimating accumulation of dirt in a filter.

BACKGROUND INFORMATION

Fans and blowers are known to be used in ventilation applications. They can consume a large share of all electrical energy used in the industry and service sectors. A majority of life-cycle costs of a fan system can be energy costs.

In a ventilation application, the fan system can be equipped with an air filter, for example, to maintain performance of a heat exchanger. The filter can cause an additional pressure drop in the ventilation system, thus, decreasing the efficiency of the fan system. The efficiency can, for example, be represented by the specific fan power SFP (kW/m³/s) which represents power consumption as a function of the flow rate. For known fine filters, an initial pressure drop can, for example, be approximately 50 to 100 Pa when the final pressure at the time of filter change is 200 to 250 Pa. According to the publication *Recommendation Concerning Calculating Life Cycle Cost for Air Filters*, Eurovent, September, 2005, a filters can be responsible for a large portion of total pressure drop in ventilation systems.

Condition monitoring of an air filter can be carried out by measuring a pressure difference over the air filter. FIG. 1 illustrates an exemplary ventilation fan 10 with an air filter 11. The condition of the air filter can be monitored by a pressure difference measurement 12. An increasing pressure difference can indicate accumulation of dirt in the air filter 11.

This can determine the filter condition but uses extra instrumentation, thus, increasing cost of the system. A related issue is that the pressure loss of the air filter 12 can be influenced by the flow rate through the filter.

In an exemplary embodiment of a method according to the disclosure, accumulation of dirt on an air filter in a ventilation system including the filter and a fan can be accurately detected under different operating conditions.

An amount of dirt in the filter can be estimated on the basis of the effect the dirt has on the operating point of the fan. The operating point can be estimated on the basis of characteristics curves and power of the fan. The power can be estimated on the basis of a mechanical torque and a rotational speed of the fan.

On the basis of the operating point, a filter pressure loss induced by the dirt can be estimated. A specific fan power representing power consumption in respect of a flow rate through the fan can also be calculated on the basis of the operating point. In an exemplary embodiment of a method according to the disclosure, a power loss induced by the dirt accumulating on the filter can be calculated on the basis of the operating point.

Exemplary embodiments of the disclosure are able to accurately detect accumulation of dirt even if the fan system operates under different operating conditions. The accumulation of dirt can be estimated without cost-increasing pressure sensors.

SUMMARY

A method is disclosed for monitoring accumulation of dirt on an air filter of a ventilation system including the air filter and a fan controlled by a frequency converter, the method comprising: determining an initial value for an operating parameter, including at least one of a dynamic resistance of the fan and a specific fan power consumption; determining characteristic curves of the fan; determining a torque and a rotational speed of the fan; estimating a mechanical power of the fan based on the torque and the rotational speed; determining a present operating point based on the characteristic curves, the mechanical power, and the rotational speed; determining a present value for the operating parameter based on the present operating point; and determining accumulation of dirt on the air filter on the basis of the initial and present values of the operating parameter.

An apparatus for monitoring accumulation of dirt on an air filter of a ventilation system including a filter and a fan controlled by a frequency converter, wherein the apparatus comprises a processor coupled to a memory configured to: determine an initial value for an operating parameter, including at least one of a dynamic resistance of a fan system and fan power consumption; determine characteristic curves of the fan; determine the torque and rotational speed of the fan; estimate a mechanical power of the fan based on the torque and the rotational speed; determine a present operating point based on the characteristic curves, the mechanical power; and the rotational speed; determine a present value for the operating parameter based on the present operating point; and determine accumulation of dirt on an air filter based on the initial and present values of the operating parameter.

BRIEF DESCRIPTION OF THE DRAWINGS

In the following, the disclosure will be described in greater detail by exemplary embodiments with reference to the attached drawings, in which.

DETAILED DESCRIPTION

The following paragraphs disclose exemplary embodiments of methods and apparatus for monitoring accumulation of dirt on an air filter of a ventilation system including an air filter and a fan controlled by a frequency converter. An amount of dirt in the filter can be estimated on the basis of the effect the dirt has on the operating point of the fan.

The accumulated dirt can be considered to influence the operating point through its effect on a process curve of the ventilation system. The process curve describes the pressure difference (system losses) p over the system as a function of the flow rate Q through the system. The losses can originate from piping, adjustment valves and air filters. These losses can be modelled to be proportional to the square of the flow rate Q. Because the static pressure over the system can be considered insignificant for the calculations, the process curve can be formulated as follows:

$$p = kQ^2, \quad (1)$$

where k is a dynamic resistance factor representing all losses in the system.

The operating point of a fan system is located at the intersection of a Qp-characteristics curve of the fan and the process curve. The Qp-characteristics curve represents a relation between flow rate and pressure at a certain rotational speed. The dynamic resistance factor increases as dirt accumulates on an air filter. A change in the dynamic resistance causes a change in the process curve, and, as a consequence, the location of the intersection the Qp-characteristics curve and the process curve. In other words, the operating point shifts.

Figure 1:
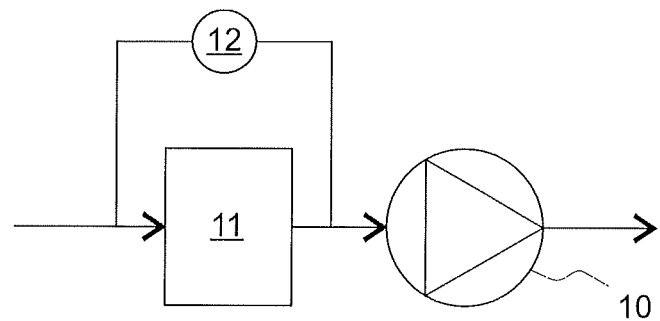
FIG. 1 illustrates an example of a ventilation fan with an air filter.
Figure 2:
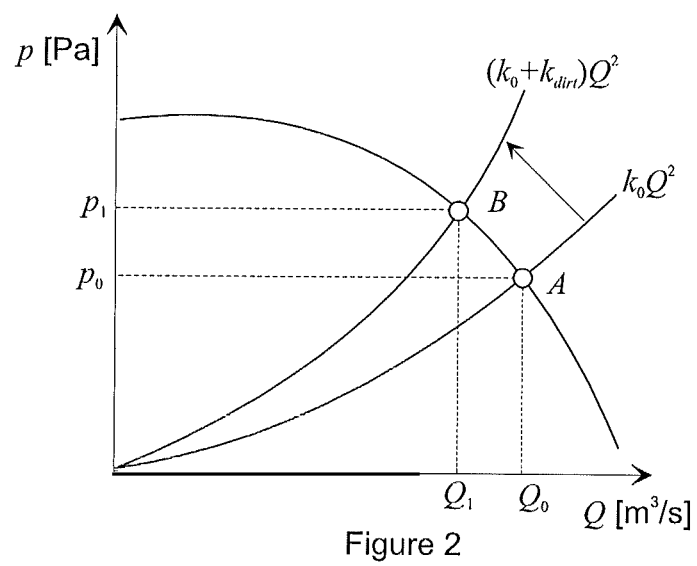
FIG. 2 illustrates an effect accumulating dirt has on the process curve of an exemplary fan system.

FIG. 2 illustrates an effect accumulating dirt has on the process curve of an exemplary fan system. In FIG. 2, an initial value A for the operating point of the fan system is illustrated at the intersection of the Qp-characteristics curve at the used rotational speed and the initial process curve with an initial dynamic resistance factor $k_0$. In the operating point A, a flow rate $Q_0$ produces a pressure difference $p_0$.

Because of accumulating dirt, the dynamic resistance factor increases to value $k_0 + k_{dirt}$. When the rotational speed is assumed to remain the same, the operating point moves to the new intersection B of the process curve and the characteristics curve. In FIG. 2, increase $k_{dirt}$ in the dynamic resistance causes the operation point to move so that the flow rate decreases (to value $Q_1$) and the pressure difference increases (to value $p_1$).

The operating point of a fan can be estimated by using characteristic curves of the fan and the power of the fan. The power $P_{est}$ can be estimated on the basis of the present mechanical torque and the rotational speed of the fan.

The following equation can, for example be used:

$$P_{est} = 2\pi \frac{n_{est}}{60} T_{est}, \quad (2)$$

where $n_{est}$ is an estimated rotational speed and $T_{est}$ is an estimated torque. These estimates can be available from the frequency converter.

The characteristics curves can include the Qp-characteristics curve and a QP-characteristics curve which represents a relation between flow rate and power. The QP-characteristics curve and the Qp-characteristics curve can both be single curves representing the fan characteristics at a certain rotational speed, or one or both of them can be sets of curves representing the fan characteristics at a plurality of rotational speeds.

However, the fan can operate on other rotational speeds than what is given in the characteristics curves. In order to enable estimation of the operating point at an arbitrary rotational speed, the fan characteristics curves can be converted to represent the present rotational speed n by using the affinity laws:

$$Q = \frac{n}{n_0} Q_0, \quad (3)$$

$$p = \left(\frac{n}{n_0}\right)^2 p_0, \text{ and} \quad (4)$$

$$P = \left(\frac{n}{n_0}\right)^3 P_0, \quad (5)$$

where the subscript $_0$ denotes nominal values used in the characteristics curves.

Figure 3A:
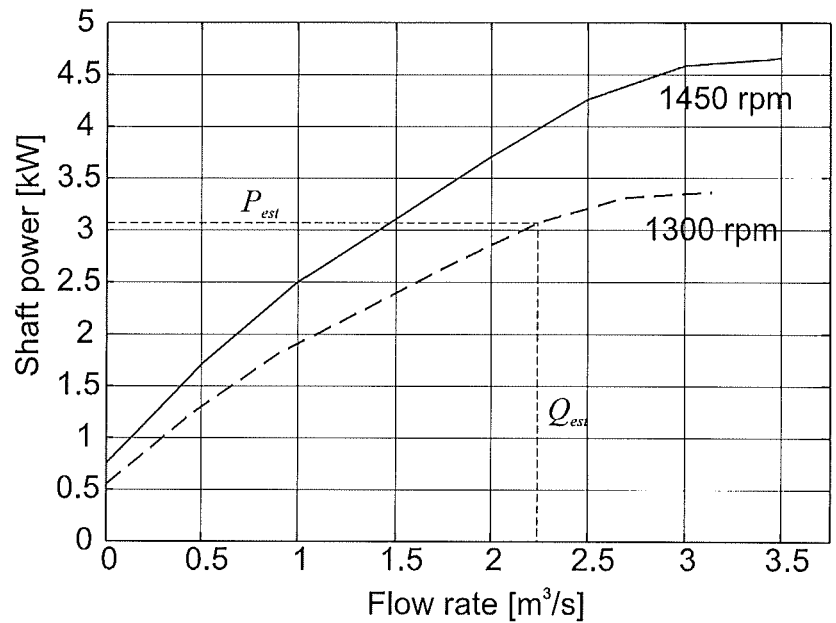
FIGS. 3a and 3b illustrate characteristics curves according to an exemplary embodiment of the disclosure.
Figure 3B:
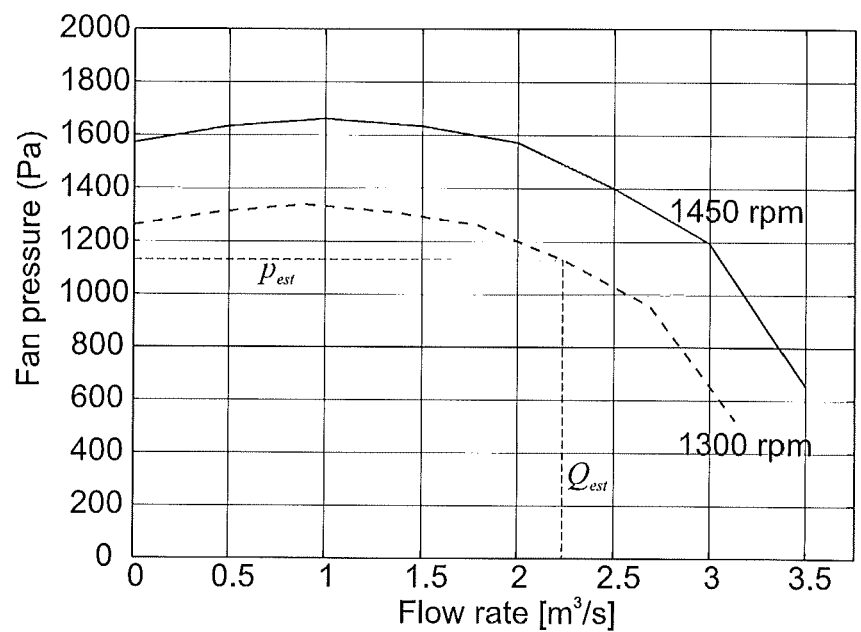

FIGS. 3a and 3b illustrate exemplary characteristics curves. In FIGS. 3a and 3b, curves at nominal rotational speeds are illustrated using a solid line. Curves calculated using the affinity laws are illustrated with a dashed line.

In order to determine the operating point, a flow rate through the filter and the fan can be estimated on the basis of the mechanical power, the rotational speed, and a QP-characteristics curve. FIG. 3a shows a QP-characteristics curve from which the flow rate can be determined.

Determining the operating point can also include estimating a pressure difference over the filter system on the basis of the estimated flow rate, the rotational speed, and a Qp-characteristics curve. The pressure difference can, for example, be determined by using the Qp-characteristics curve in FIG. 3b and the determined flow rate.

The operating point can then be used to calculate values (e.g., via a processor) for some operating parameters of the fan system, such as the dynamic resistance of the fan system or a specific fan power. The air filter condition can be monitored without additional sensors by calculating an effect the movement of the operating point has on the operating parameter.

The dynamic resistance or the specific fan power consumption can by themselves serve as an indicator for accumulation of dirt. A filter pressure loss induced by the dirt can further be estimated on the basis of a change in the dynamic resistance. Alternatively, a power loss induced by the dirt accumulating on the filter can be estimated on the basis of the dynamic resistance. The estimates can, for example, be normalized to express values in relation to a nominal flow rate of the fan.

The method and apparatus according to an exemplary embodiment of the disclosure can, for example, operate as described in the following paragraphs.

Characteristics curves of the fan and the initial operating conditions can first be determined in order to be able to detect a change in operating conditions. An initial value for the operating parameter can be determined and stored (e.g., in memory) so that it can serve as a reference value representing a clean filter. The operating parameter can, for example, be the dynamic resistance of the fan system or the specific fan power consumption. The initial value for the operating parameter can, for example, be determined on the basis of an estimated initial operating point. The initial operating point can be estimated as disclosed above.

The present operating point can then be determined. The present torque and rotational speed of the fan can first be determined. A mechanical power of the fan can be estimated on the basis of the torque and the rotational speed. The present operating point can then be estimated on the basis of the characteristics curves, the mechanical power, and the present rotational speed. For example, a present flow rate through the filter and the fan can be estimated on the basis of the mechanical power, the rotational speed, and a QP-characteristics curve. A present pressure difference over the filter system can also be estimated on the basis of the estimated flow rate, the rotational speed, and a Qp-characteristics curve.

The present value for the operating parameter can then be determined on the basis of the present operating point. Finally, accumulation of dirt on the air filter can be determined on the basis of the initial and present values of the operating parameter.

Figure 4:
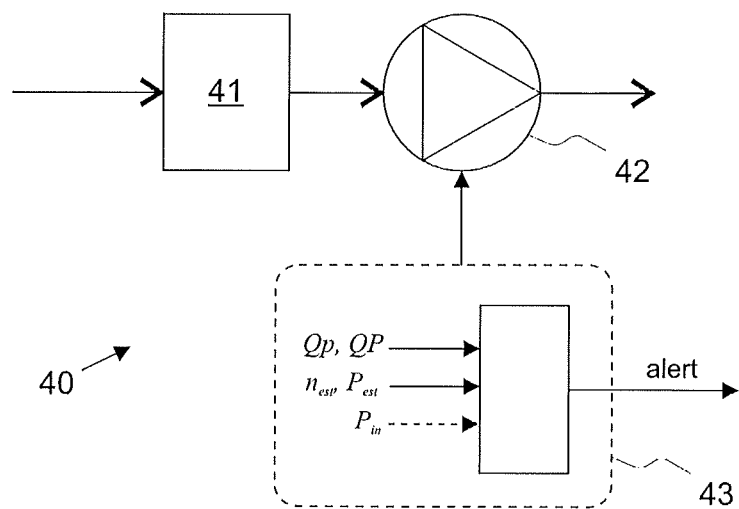
FIG. 4 illustrates an ventilation system according to an exemplary embodiment of the disclosure.

FIG. 4 illustrates an exemplary embodiment of a ventilation system 40 including an air filter 41 and a fan 42 controlled by a frequency converter 43. In FIG. 4, air travels through the air filter 41 and the fan 42. An apparatus (e.g., having a processor and memory) according to an exemplary embodiment of the disclosure is used for estimating accumulation of dirt on the air filter 41 on the basis of the effect the dirt has on the operating point of the fan 42. In FIG. 4, the apparatus is implemented in the frequency converter 43. However, in exemplary embodiments of the disclosure, the apparatus can also be a separate device.

In FIG. 4, the characteristics curves Qp and QP are determined by storing their values in the memory of the frequency converter 43. The frequency converter 43 includes a processor (e.g., hardware or software, or any combination thereof), configured to determine an initial value for the operating parameter.

In FIG. 4, an estimated torque $n_{est}$ and an estimated rotational speed $T_{est}$ are available from the frequency converter 43, and the frequency converter 43 includes a processor coupled to a memory configured to determine an estimate of a mechanical power of the fan on the basis of the torque and the rotational speed and includes a processor coupled to a memory configured to determine a present operating point on the basis of the characteristics curves, the mechanical power, and the rotational speed.

The frequency converter 43 includes a processor configured to determine the present value for the operating parameter on the basis of the present operating point, and to determine accumulation of dirt on the air filter on the basis of the initial and present values of the operating parameter. If the frequency converter 43 determines that the amount of dirt has exceeded an allowable level, it can send an alert.

In another exemplary embodiment of a method according to the disclosure, the specific fan power consumption can be used as the operating parameter. Determining the present operating point can include a previously disclosed step of estimating the flow rate. The present specific fan power consumption SFP can be estimated on the basis of the estimated flow rate Q and the mechanical power P as follows:

$$SFP = \frac{P}{Q} \quad (6)$$

Because the specific fan power consumption is dependent on the rotational speed, it can in some cases be useful to include the rotational speed n in Equation 5:

$$SFP_0 = \left(\frac{n_0}{n}\right)^2 SFP, \quad (7)$$

where $n_0$ is the nominal rotational speed. Accumulation of dirt on the air filter can be determined by calculating a difference between the initial specific fan power consumption and the present specific fan power. The calculated difference can be compared to a set limit, and the accumulation of dirt can finally be determined on the basis of the comparison result. For example, if the value of the SFP exceeds the set limit, the method or apparatus of exemplary embodiments of the disclosure can detect that a certain level of dirt has accumulated in the filter and inform the maintenance personnel.

In another exemplary embodiment according to the disclosure, the operating parameter can represent the dynamic resistance. In order to calculate the dynamic resistance, the embodiment performs the previously disclosed steps for estimating the flow rate and the pressure difference.

The present value for the operating parameter can then be determined by estimating the dynamic resistance on the basis of the estimated flow rate $Q_{est}$ and pressure difference $p_{est}$. The dynamic resistance k can, for example be calculated at any rotational speed as follows:

$$k = \frac{p_{est}}{Q_{est}^2}, \quad (8)$$

assuming that a static pressure over the system can, be considered insignificant.

When dirt accumulates on the filter, the system dynamic resistance increases, as illustrated in FIG. 3. Thus, determining accumulation of dirt on the air filter can include calculating a change in the dynamic resistance induced by the dirt on the basis of the initial dynamic resistance and the present dynamic resistance, wherein the initial dynamic resistance represents the system resistance in a system with a clean filter. The calculated change can be compared to a set limit, and accumulation of dirt can be directly determined on the basis of the comparison result.

Alternatively, determining accumulation of dirt on the air filter can be done by estimating a present pressure loss $p_{d,dirt}$ over the filter induced by the dirt at a nominal flow rate $Q_{nom}$ on the basis of a difference between the initial dynamic resistance $k_0$, the present dynamic resistance k, and the nominal flow rate $Q_{nom}$ as follows:

$$P_{d,dirt} = (k-k_0)Q_{nom}^2 = k_{dirt}Q_{nom}^2. \quad (9)$$

The dynamic resistance difference $k_{dirt}$ represents the difference between the initial and present dynamic resistance induced by the dirt.

The estimated pressure loss $p_{d,dirt}$ can be compared with a set limit, and accumulation of dirt can be determined on the basis of the comparison result. For example, if the calculated pressure loss exceeds 150 Pa, the method or apparatus can inform maintenance personnel that the filter should be cleaned or changed.

In an exemplary embodiment of the disclosure, a power loss $P_{loss,dirt}$ induced by the dirt at a nominal rotational speed $n_0$ is calculated on the basis of the dynamic resistance difference $k_{dirt}$ induced by the dirt. The increased system pressure requirement induced by the accumulated dirt also increases power requirement of the fan, the motor, and the frequency converter (e.g., an inverter). Determining accumulation of dirt can, thus, be performed by estimating the power loss $p_{loss,dirt}$ on the basis of the present dynamic resistance k, the dynamic resistance difference $k_{dirt}$, the nominal rotational speed $n_0$, the present rotational speed n and an electric power $P_{in}$ consumed by the frequency converter, for example, as follows:

$$P_{loss,dirt} = \frac{k_{dirt}}{k}\left(\frac{n_0}{n}\right)^3 P_{in}. \quad (10)$$

The power loss can then be compared with a set limit, and the accumulation of dirt can be determined on the basis of the comparison result.

Laboratory measurements were conducted with a radial fan system including a FläktWoods Centripal EU 4 MD 630 radial blower, an ABB induction motor and an ABB ACS 850 frequency converter. The fan had the following nominal values: rotational speed 1446 rpm, power 7.5 kW, flow rate 2.90 m³/s, fan total pressure 1190 Pa, and impeller diameter 630 mm. The nominal values of the motor were: rotational speed 1450 rpm, power 7.5 kW, current 15.7 A, and cos $\phi$ 0.80. The nominal current of the frequency converter was 16 A.

Accumulation of dirt in the filter was simulated by closing a control valve, which caused an increase in the system dynamic resistance in the similar manner as a dirty filter would have caused. At the rotational speed of 1500 rpm, the resulting pressure drop was 50 Pa, which was in a same magnitude range as a typical pressure loss (150 Pa) of a dirty filter.

However, the estimated dynamic resistances of the clean filter and the dirty remained comparable with each other. The disclosed method can thus be used for estimating accumulation of dirt by comparing the two dynamic resistances. Between a clear filter and a dirty filter, a clear change in the dynamic resistance and pressure loss can be observed in Table 1.

Table 2 shows the estimated specific fan power $SFP_0$. Accumulation of dirt caused a significant change in the estimated specific fan power $SFP_0$ at every rotational speed of Table 2.

TABLE 2

| | Rotational speed (rpm) | | | | | | | | | |
|---|---|---|---|---|---|---|---|---|---|---|
| | 600 | 750 | 900 | 1050 | 1200 | 1350 | 1500 | 1650 | 1800 | Measured |
| $SFP_0$ clean | 2.2 | 2.3 | 2.4 | 2.4 | 2.4 | 2.5 | 2.4 | 2.6 | 2.6 | 2.4 |
| $SFP_0$ dirty | 2.6 | 2.8 | 3.0 | 3.1 | 3.1 | 3.2 | 3.3 | 3.5 | 3.8 | 3.2 |
| $\Delta SFP_0$ | 0.4 | 0.5 | 0.6 | 0.7 | 0.7 | 0.7 | 0.9 | 1.1 | 1.2 | 0.8 |

Figure 5:
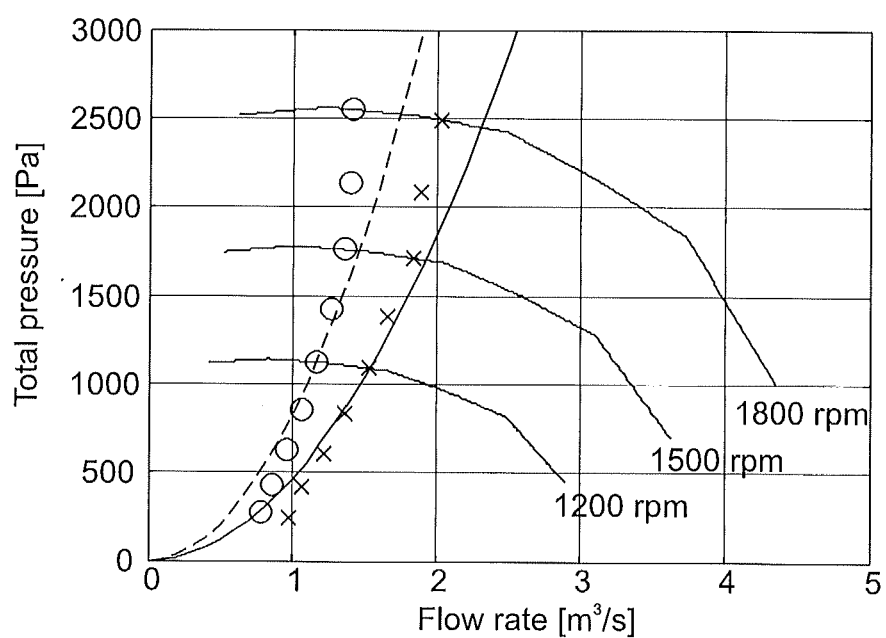
FIG. 5 illustrates measurement results.

FIG. 5 illustrates measurement results. An actual process curve of the system with a clean filter is illustrated using a dashed line. Small crosses show estimated operating points with a clean filter. An actual process curve of the system with a dirty filter is illustrated using a solid line. Small circles show estimated operating points with a dirty filter.

It can be seen from FIG. 5 that the flow rate estimation gave too high values when the fan was operating at low rotational speeds (<1000 rpm). At rotational speeds above 1500 rpm, it gave too low values for the flow rate. This was due to the affinity laws (Equations 3 to 5). The affinity laws can give an accurate estimate when the present rotational speed deviates from the rotational speed of the characteristics curve less than 10%. The rotational speed also affected the estimation of the dynamic resistance through the inaccurate flow rate estimates.

Table 1 shows the system dynamic resistance and pressure loss at different rotational speeds. The pressure loss was calculated for a nominal flow of 1.5 m$^3$/s. The estimated dynamic resistance clearly changed responsive to the rotational speed even though the actual dynamic resistance stayed the same. The pressure loss is directly dependent on the dynamic resistance, so the pressure loss estimates were not the same at different rotational speeds but changed together with the dynamic resistance.

However, the specific fan power of a clean filter at 1800 rpm was the same as the specific fan power of the dirty filter at 600 rpm. Thus, it was difficult to establish a single triggering limit for the specific fan power indicating a dirty filter for all rotational speeds used in the simulation. The different values in the estimated specific fan powers were, again, caused by the inaccuracy in estimating the flow rate.

In order to improve accuracy, the characteristics curves and the estimation of the dynamic resistance can be divided into separate rotational speed zones. For example, the characteristic curves can be represented by two sets of curves. The curves in each set of curves can, for example, be less than 10% of their nominal rotational speed apart from their adjacent curves. When estimating the flow, the curve in a set of characteristics curves having the closest matching rotational speed can first be selected and then the affinity laws together with the actual rotational speed can be used for calculating the flow rate.

Finally, the estimated power loss at flow rate 1.5 m$^3$/s is shown in Table 3.

TABLE 1

| | Rotational speed (rpm) | | | | | | | | | |
|---|---|---|---|---|---|---|---|---|---|---|
| | 600 | 750 | 900 | 1050 | 1200 | 1350 | 1500 | 1650 | 1800 | Measured |
| Clean filter k (Pa · s$^2$/m$^6$) | 260 | 360 | 408 | 452 | 468 | 505 | 508 | 585 | 606 | 461 |
| Dirty filter k (Pa · s$^2$/m$^6$) | 432 | 578 | 670 | 749 | 813 | 872 | 954 | 1098 | 1270 | 827 |
| $\Delta k$ | 172 | 219 | 262 | 297 | 345 | 368 | 446 | 512 | 664 | 365 |
| $p_{d,dirt}$ (Pa) | 388 | 492 | 589 | 669 | 776 | 827 | 1004 | 1153 | 1495 | 821 |

TABLE 3

| | Rotational speed (rpm) | | | | | | | | | |
|---|---|---|---|---|---|---|---|---|---|---|
| | 600 | 750 | 900 | 1050 | 1200 | 1350 | 1500 | 1650 | 1800 | Measured |
| $P_{loss,dirt}$ (kW) | 2.0 | 1.8 | 1.8 | 1.8 | 1.9 | 1.9 | 2.0 | 2.0 | 2.2 | 2.2 |

The increase on the power loss is apparent at every rotational speed, and, thus, it can directly be used as an indicator of dirt in the filter.

Exemplary embodiments of the present disclosure have been described with respect to the operative features the structural components perform. The exemplary embodiments of the present disclosure can be implemented by at least one processor (e.g., hardware or software, or any combination thereof) and/or a computer processing device which is configured to execute a computer program tangibly recorded on a non-transitory computer-readable recording medium, such as a hard disk drive, flash memory, optical memory or any other type of non-volatile memory. Upon executing the program, the at least one processor is configured to perform the operative functions of the above-described exemplary embodiments.

Thus, it will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. A method for monitoring accumulation of dirt on an air filter of a ventilation system including the air filter and a fan controlled by a frequency converter, the method comprising:
determining an initial value for an operating parameter, including at least one of a dynamic resistance of the fan and specific fan power consumption;
determining characteristic curves of the fan;
determining a torque and a rotational speed of the fan;
estimating a mechanical power of the fan based on the torque and the rotational speed;
determining a present operating point based on the characteristic curves, the mechanical power, and the rotational speed;
determining a present value for the operating parameter based on the present operating point; and
determining accumulation of dirt on the air filter on the basis of the initial and present values of the operating parameter.

2. The method according to claim 1, wherein determining the present operating point comprises:
estimating a flow rate through the air filter and the fan based on the mechanical power, the rotational speed, and a QP-characteristics curve.

3. The method according to claim 2, wherein determining the present operating point comprises:
estimating a pressure difference over the air filter based on the estimated flow rate, the rotational speed, and a Qp-characteristics curve.

4. The method according to claim 2, wherein determining the present value for the operating parameter comprises:
estimating a specific fan power consumption based on the estimated flow rate and the mechanical power; and
wherein determining accumulation of dirt on the air filter comprises:
calculating a difference between initial specific fan power consumption and present specific fan power consumption;
comparing the calculated difference to a set limit; and
determining the accumulation of dirt based on the comparison result.

5. A method according to claim 3, wherein determining the present value for the operating parameter comprises:
estimating dynamic resistance based on the flow rate and the pressure difference.

6. A method according to claim 5, wherein determining accumulation of dirt on the air filter comprises:
calculating a change in the dynamic resistance induced by dirt from an initial dynamic resistance and a present dynamic resistance;
comparing the change to a set limit; and
determining the accumulation of dirt based on the comparison result.

7. A method according to claim 5, wherein determining accumulation of dirt on the air filter comprises:
estimating a pressure loss over the filter induced by the dirt at a nominal flow rate based on a difference between an initial dynamic resistance, a present dynamic resistance, and a nominal flow rate;
comparing the estimated pressure loss to a set limit; and
determining the accumulation of dirt based on a result of the comparison.

8. A method according to claim 5, wherein determining accumulation of dirt on the air filter comprises:
estimating a power loss induced by the dirt at a nominal rotational speed based on a present dynamic resistance, a dynamic resistance difference between an initial dynamic resistance and the present dynamic resistance, a nominal and present rotational speed, and an electric power consumed by the frequency converter;
comparing the power loss to a set limit; and
determining the accumulation of dirt based on the comparison result.

9. An apparatus for monitoring accumulation of dirt on an air filter of a ventilation system including a filter and a fan controlled by a frequency converter, wherein the apparatus comprises a processor coupled to a memory configured to:
determine an initial value for an operating parameter, including at least one of a dynamic resistance of a fan system and fan power consumption;
determine characteristic curves of the fan;
determine the torque and rotational speed of the fan;
estimate a mechanical power of the fan based on the torque and the rotational speed;
determine a present operating point based on the characteristic curves, the mechanical power; and the rotational speed;
determine a present value for the operating parameter based on the present operating point; and
determine accumulation of dirt on an air filter based on the initial and present values of the operating parameter.

10. The apparatus according to claim 9, wherein the processor and memory are configured to determine the present operating point by:

estimating a present flow rate through the filter and the fan based on the mechanical power, the rotational speed, and a QP-characteristics curve.

11. The apparatus according to claim 10, wherein the processor and memory are configured to determine the present operating point by:

estimating a present pressure difference over a filter based on the estimated flow rate, the rotational speed, and a Qp-characteristics curve.

12. The apparatus according to claim 10, wherein the processor and memory are configured to determine the present value for the operating parameter by:

estimating a present fan power consumption based on the estimated flow rate and the mechanical power; and are configured to determine accumulation of dirt on an air filter by:

calculating a difference between initial specific fan power consumption and present specific fan power consumption;

comparing the calculated difference to a set limit; and determining an accumulation of dirt based on a result of comparison.

13. The apparatus according to claim 11, wherein the processor and memory are configured to determine the present value for the operating parameter by:

estimating dynamic resistance based on the flow rate and the pressure difference.

14. The apparatus according to claim 13, wherein the processor and memory are configured to determine accumulation of dirt on the air filter by:

calculating a change in the dynamic resistance induced by dirt from an initial dynamic resistance and a present dynamic resistance;

comparing the change to a set limit; and determining accumulation of dirt based on a result of the comparison.

15. The apparatus according to claim 13, wherein the processor and memory are configured to determine accumulation of dirt on an air filter by:

estimating a present pressure loss over the filter induced by dirt at a nominal flow rate based on a difference between an initial dynamic resistance, a present dynamic resistance, and a nominal flow rate, comparing the estimated present pressure loss to a set limit; and determining the accumulation of dirt based on a result of the comparison.

16. The apparatus according to claim 13, wherein the processor and memory are configured to determine accumulation of dirt on the air filter by:

estimating a power loss induced by dirt at a nominal rotational speed based on a present dynamic resistance, a dynamic resistance difference between an initial dynamic resistance and present dynamic resistance, a nominal and present rotational speed, and an electric power consumed by the frequency converter;

comparing the power loss to a set limit; and determining accumulation of dirt based on a result of the comparison.

* * * * *